US008123758B2

(12) United States Patent
Metzger et al.

(10) Patent No.: US 8,123,758 B2
(45) Date of Patent: *Feb. 28, 2012

(54) FEMORAL GUIDE FOR IMPLANTING A FEMORAL KNEE PROSTHESIS

(75) Inventors: Robert Metzger, Wakarusa, IN (US); Jacy C. Hoeppner, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 471 days.

This patent is subject to a terminal disclaimer.

(21) Appl. No.: 12/367,903

(22) Filed: Feb. 9, 2009

(65) Prior Publication Data

US 2009/0149859 A1   Jun. 11, 2009

Related U.S. Application Data

(63) Continuation of application No. 10/730,456, filed on Dec. 8, 2003, now Pat. No. 7,488,324.

(51) Int. Cl.
    *A61B 17/58* (2006.01)
(52) U.S. Cl. ...................................................... 606/102
(58) Field of Classification Search .............. 606/86–89, 606/96, 102; 33/511–512
    See application file for complete search history.

(56) References Cited

U.S. PATENT DOCUMENTS

| | | |
|---|---|---|
| 1,763,730 A | 6/1930 | Von Lackum |
| 1,959,615 A | 5/1934 | Derrah |
| 2,433,815 A | 12/1947 | LaForge |
| 2,455,655 A | 12/1948 | Carroll |
| 2,702,550 A | 2/1955 | Rowe |
| 2,724,326 A | 11/1955 | Long |
| 2,955,530 A | 10/1960 | Nilo |
| 3,048,522 A | 8/1962 | Velley |
| 3,229,006 A | 1/1966 | Nohl |
| 3,514,791 A | 6/1970 | Sparks |
| 3,554,197 A | 1/1971 | Dobbie et al. |
| 3,624,747 A | 11/1971 | McKnight et al. |
| 3,631,596 A | 1/1972 | Glaus et al. |
| 3,678,934 A | 7/1972 | Warfield et al. |
| 3,698,017 A | 10/1972 | Scales et al. |
| 3,703,036 A | 11/1972 | Karubian |
| 3,774,244 A | 11/1973 | Walker |
| 3,783,873 A | 1/1974 | Jacobs |
| 3,807,393 A | 4/1974 | McDonald |

(Continued)

FOREIGN PATENT DOCUMENTS

CH     117960     5/1927

(Continued)

OTHER PUBLICATIONS

"NexGen® Complete Knee Solution MIS Quad-Sparing™ Instrumentation," (Mar. 17, 2006) Zimmer, Inc. Web. Jul. 21, 2010. http://www.zimmer.com/ctl?prcat=M3&prod=y&template=MP&action=1&op=global&id... 2 pages.

(Continued)

*Primary Examiner* — William H. Matthews
(74) *Attorney, Agent, or Firm* — Harness, Dickey

(57) ABSTRACT

Disclosed is a modular femoral sizing guide which facilitates the selection and rotational orientation of a femoral prosthetic for a resected femur. The femoral sizing guide has a base which is coupled to the resected femur. An extension portion which is configured to have a pair of feet which are coupled to the posterior surface of the resected femur is rotatably coupled to the base portion. A superstructure having a pair of drilling guides and a stylus is slidably coupled to the base.

21 Claims, 9 Drawing Sheets

U.S. PATENT DOCUMENTS

| | | |
|---|---|---|
| 3,811,449 A | 5/1974 | Gravlee et al. |
| 3,869,731 A | 3/1975 | Waugh et al. |
| 3,903,549 A | 9/1975 | Deyerle |
| 3,905,105 A | 9/1975 | Tuke et al. |
| 3,905,374 A | 9/1975 | Winter |
| 3,911,923 A | 10/1975 | Yoon |
| 3,913,585 A | 10/1975 | Wolvek |
| 3,920,022 A | 11/1975 | Pastor |
| 3,941,127 A | 3/1976 | Froning |
| 3,967,625 A | 7/1976 | Yoon |
| 3,989,049 A | 11/1976 | Yoon |
| 3,991,426 A | 11/1976 | Flom et al. |
| 3,994,287 A | 11/1976 | Turp et al. |
| 4,053,953 A | 10/1977 | Flom et al. |
| 4,055,862 A | 11/1977 | Farling |
| 4,081,866 A | 4/1978 | Upshaw et al. |
| 4,085,466 A | 4/1978 | Goodfellow et al. |
| 4,085,743 A | 4/1978 | Yoon |
| 4,103,680 A | 8/1978 | Yoon |
| 4,299,224 A | 11/1981 | Noiles |
| 4,304,178 A | 12/1981 | Haberle et al. |
| 4,311,145 A | 1/1982 | Esty et al. |
| 4,344,193 A | 8/1982 | Kenny |
| 4,349,018 A | 9/1982 | Chambers |
| 4,373,709 A | 2/1983 | Whitt |
| 4,374,523 A | 2/1983 | Yoon |
| 4,385,404 A | 5/1983 | Sully et al. |
| 4,386,609 A | 6/1983 | Mongeon |
| 4,400,833 A | 8/1983 | Kurland |
| D273,895 S | 5/1984 | Kenna |
| D274,091 S | 5/1984 | Kenna |
| 4,453,421 A | 6/1984 | Umano et al. |
| 4,501,269 A | 2/1985 | Bagby |
| 4,509,518 A | 4/1985 | McGarry et al. |
| 4,516,276 A | 5/1985 | Mittelmeier et al. |
| 4,534,365 A | 8/1985 | Bonetta et al. |
| 4,545,375 A | 10/1985 | Cline |
| 4,554,686 A | 11/1985 | Baker |
| 4,562,598 A | 1/1986 | Kranz et al. |
| 4,565,192 A | 1/1986 | Shapiro |
| 4,567,886 A | 2/1986 | Petersen |
| 4,574,794 A | 3/1986 | Cooke et al. |
| 4,619,391 A | 10/1986 | Sharkany et al. |
| 4,624,254 A | 11/1986 | McGarry et al. |
| 4,641,648 A | 2/1987 | Shapiro |
| 4,642,120 A | 2/1987 | Nevo et al. |
| 4,646,729 A | 3/1987 | Kenna et al. |
| 4,662,372 A | 5/1987 | Sharkany et al. |
| 4,678,470 A | 7/1987 | Nashef et al. |
| 4,682,598 A | 7/1987 | Beraha |
| 4,685,460 A | 8/1987 | Thornton |
| 4,703,751 A | 11/1987 | Pohl |
| 4,711,233 A | 12/1987 | Brown |
| 4,718,413 A | 1/1988 | Johnson |
| 4,718,916 A | 1/1988 | Morscher et al. |
| 4,739,751 A | 4/1988 | Sapega et al. |
| 4,794,854 A | 1/1989 | Swaim |
| 4,817,602 A | 4/1989 | Beraha |
| 4,834,757 A | 5/1989 | Brantigan |
| 4,838,891 A | 6/1989 | Branemark et al. |
| 4,863,472 A | 9/1989 | Tormala et al. |
| 4,888,022 A | 12/1989 | Huebsch |
| 4,911,721 A | 3/1990 | Andergaten, III et al. |
| 4,935,023 A | 6/1990 | Whiteside et al. |
| 4,936,852 A | 6/1990 | Kent et al. |
| 4,950,296 A | 8/1990 | McIntyre |
| 4,952,213 A | 8/1990 | Bowman et al. |
| 4,961,740 A | 10/1990 | Ray et al. |
| 4,961,954 A | 10/1990 | Goldberg et al. |
| 4,964,865 A | 10/1990 | Burkhead et al. |
| 4,979,949 A | 12/1990 | Matsen, III et al. |
| 4,979,957 A | 12/1990 | Hodorek |
| 4,985,038 A | 1/1991 | Lyell |
| 5,007,912 A | 4/1991 | Albrektsson et al. |
| 5,015,247 A | 5/1991 | Michelson |
| 5,032,132 A | 7/1991 | Matsen, III et al. |
| 5,035,700 A | 7/1991 | Kenna |
| 5,060,678 A | 10/1991 | Bauman et al. |
| 5,061,286 A | 10/1991 | Lyle |
| 5,062,843 A | 11/1991 | Mahony, III |
| 5,073,373 A | 12/1991 | O'Leary et al. |
| 5,082,670 A | 1/1992 | Gage et al. |
| 5,084,050 A | 1/1992 | Draenert et al. |
| 5,092,869 A | 3/1992 | Waldron |
| 5,098,436 A | 3/1992 | Ferrante et al. |
| 5,098,437 A | 3/1992 | Kashuba et al. |
| 5,099,859 A | 3/1992 | Bell |
| 5,100,689 A | 3/1992 | Goldberg et al. |
| 5,101,720 A | 4/1992 | Bianchi |
| 5,108,441 A | 4/1992 | McDowell |
| 5,111,987 A | 5/1992 | Moeinzadeh et al. |
| 5,122,144 A | 6/1992 | Bert et al. |
| 5,123,906 A | 6/1992 | Kelman |
| 5,129,909 A | 7/1992 | Sutherland |
| 5,147,365 A | 9/1992 | Whitlock et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,162,506 A | 11/1992 | Hadden et al. |
| 5,163,949 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,702 A | 1/1993 | Bales et al. |
| 5,178,622 A | 1/1993 | Lehner, II |
| 5,183,053 A | 2/1993 | Yeh et al. |
| 5,183,464 A | 2/1993 | Dubrul et al. |
| 5,186,178 A | 2/1993 | Yeh et al. |
| 5,192,327 A | 3/1993 | Brantigan |
| 5,197,968 A | 3/1993 | Clement |
| 5,197,971 A | 3/1993 | Bonutti |
| 5,197,987 A | 3/1993 | Koch et al. |
| 5,204,106 A | 4/1993 | Schepers et al. |
| 5,207,680 A | 5/1993 | Dietz et al. |
| 5,207,692 A | 5/1993 | Kraus et al. |
| 5,217,463 A | 6/1993 | Mikhail |
| 5,228,459 A | 7/1993 | Caspari et al. |
| 5,234,433 A | 8/1993 | Bert et al. |
| 5,242,448 A | 9/1993 | Pettine et al. |
| 5,258,004 A | 11/1993 | Bales et al. |
| 5,263,498 A | 11/1993 | Caspari et al. |
| 5,263,987 A | 11/1993 | Shah |
| 5,269,785 A | 12/1993 | Bonutti |
| 5,273,524 A | 12/1993 | Fox et al. |
| D343,247 S | 1/1994 | Walen |
| 5,275,166 A | 1/1994 | Vaitekunas et al. |
| 5,275,603 A | 1/1994 | Ferrante et al. |
| 5,282,803 A | 2/1994 | Lackey |
| 5,285,773 A | 2/1994 | Bonutti et al. |
| 5,293,878 A | 3/1994 | Bales et al. |
| 5,295,994 A | 3/1994 | Bonutti |
| 5,304,181 A | 4/1994 | Caspari et al. |
| 5,306,285 A | 4/1994 | Miller et al. |
| 5,308,349 A | 5/1994 | Mikhail |
| 5,314,482 A | 5/1994 | Goodfellow et al. |
| 5,322,505 A | 6/1994 | Krause et al. |
| 5,329,845 A | 7/1994 | Bichel |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,348,541 A | 9/1994 | Lyell |
| 5,364,402 A | 11/1994 | Mumme et al. |
| 5,368,599 A | 11/1994 | Hirsch et al. |
| 5,379,133 A | 1/1995 | Kirk |
| 5,382,249 A | 1/1995 | Fletcher |
| 5,383,937 A | 1/1995 | Mikhail |
| 5,390,683 A | 2/1995 | Pisharodi |
| 5,395,376 A | 3/1995 | Caspari et al. |
| D358,647 S | 5/1995 | Cohen et al. |
| 5,423,827 A | 6/1995 | Mumme et al. |
| 5,425,355 A | 6/1995 | Kulick |
| 5,425,745 A | 6/1995 | Green et al. |
| 5,443,475 A | 8/1995 | Auerbach et al. |
| 5,445,639 A | 8/1995 | Kuslich et al. |

| Patent | Date | Inventor |
|---|---|---|
| 5,445,642 A | 8/1995 | McNulty et al. |
| 5,454,365 A | 10/1995 | Bonutti |
| 5,454,815 A | 10/1995 | Geisser et al. |
| 5,454,816 A | 10/1995 | Ashby et al. |
| 5,456,268 A | 10/1995 | Bonutti |
| 5,472,415 A | 12/1995 | King et al. |
| 5,484,095 A | 1/1996 | Green et al. |
| 5,486,178 A | 1/1996 | Hodge |
| 5,490,854 A | 2/1996 | Fisher et al. |
| 5,497,933 A | 3/1996 | DeFonzo et al. |
| 5,507,763 A | 4/1996 | Petersen et al. |
| 5,514,139 A | 5/1996 | Goldstein et al. |
| 5,514,143 A | 5/1996 | Bonutti et al. |
| 5,520,692 A | 5/1996 | Ferrante |
| 5,520,694 A | 5/1996 | Dance et al. |
| 5,522,897 A | 6/1996 | King et al. |
| 5,540,695 A | 7/1996 | Levy |
| 5,545,222 A | 8/1996 | Bonutti |
| 5,546,720 A | 8/1996 | LaBruzza |
| 5,549,683 A | 8/1996 | Bonutti |
| 5,554,169 A | 9/1996 | Green et al. |
| 5,562,675 A | 10/1996 | McNulty et al. |
| 5,569,163 A | 10/1996 | Francis et al. |
| 5,569,260 A | 10/1996 | Petersen |
| 5,569,261 A | 10/1996 | Marik et al. |
| 5,570,700 A | 11/1996 | Vogeler |
| 5,578,039 A | 11/1996 | Vendrely et al. |
| 5,593,448 A | 1/1997 | Dong |
| 5,597,379 A | 1/1997 | Haines et al. |
| 5,608,052 A | 3/1997 | Zmitek et al. |
| 5,609,603 A | 3/1997 | Linden |
| 5,624,444 A | 4/1997 | Wixon et al. |
| 5,624,463 A | 4/1997 | Stone et al. |
| 5,632,745 A | 5/1997 | Schwartz |
| 5,643,272 A | 7/1997 | Haines et al. |
| 5,649,946 A | 7/1997 | Bramlet |
| 5,649,947 A | 7/1997 | Auerbach et al. |
| 5,653,714 A | 8/1997 | Dietz et al. |
| 5,659,947 A | 8/1997 | Eilers et al. |
| 5,662,656 A | 9/1997 | White |
| 5,662,710 A | 9/1997 | Bonutti |
| 5,667,069 A | 9/1997 | Williams, Jr. |
| 5,667,511 A | 9/1997 | Vendrely et al. |
| 5,667,512 A | 9/1997 | Johnson |
| 5,667,520 A | 9/1997 | Bonutti |
| D385,163 S | 10/1997 | Hutchins et al. |
| 5,681,316 A | 10/1997 | DeOrio et al. |
| 5,683,398 A | 11/1997 | Carls et al. |
| 5,688,279 A | 11/1997 | McNulty et al. |
| 5,688,280 A | 11/1997 | Booth, Jr. et al. |
| 5,694,693 A | 12/1997 | Hutchins et al. |
| 5,702,447 A | 12/1997 | Walch et al. |
| 5,702,475 A | 12/1997 | Zahedi et al. |
| 5,704,941 A | 1/1998 | Jacober et al. |
| 5,707,350 A | 1/1998 | Krause et al. |
| 5,712,543 A | 1/1998 | Sjostrom |
| 5,716,360 A | 2/1998 | Baldwin et al. |
| 5,718,708 A | 2/1998 | Webb |
| 5,720,752 A | 2/1998 | Elliott et al. |
| 5,723,331 A | 3/1998 | Tubo et al. |
| 5,733,292 A | 3/1998 | Gustilo et al. |
| 5,749,876 A | 5/1998 | Duvillier et al. |
| 5,755,731 A | 5/1998 | Grinberg |
| 5,755,791 A | 5/1998 | Whitson et al. |
| 5,755,803 A | 5/1998 | Haines et al. |
| 5,769,855 A | 6/1998 | Bertin et al. |
| 5,769,899 A | 6/1998 | Schwartz et al. |
| 5,772,594 A | 6/1998 | Barrick |
| 5,788,700 A | 8/1998 | Morawa et al. |
| 5,810,827 A | 9/1998 | Haines et al. |
| 5,810,831 A | 9/1998 | D'Antonio |
| 5,817,097 A | 10/1998 | Howard et al. |
| 5,817,109 A | 10/1998 | McGarry et al. |
| 5,842,477 A | 12/1998 | Naughton et al. |
| 5,846,931 A | 12/1998 | Hattersley et al. |
| 5,860,980 A | 1/1999 | Axelson, Jr. et al. |
| 5,860,981 A | 1/1999 | Bertin et al. |
| 5,866,415 A | 2/1999 | Villeneuve |
| 5,871,493 A | 2/1999 | Sjostrom et al. |
| 5,879,354 A | 3/1999 | Haines et al. |
| 5,888,219 A | 3/1999 | Bonutti |
| 5,899,914 A | 5/1999 | Zirps et al. |
| 5,908,424 A | 6/1999 | Bertin et al. |
| 5,911,723 A | 6/1999 | Ashby et al. |
| 5,913,874 A | 6/1999 | Berns et al. |
| 5,916,219 A | 6/1999 | Matsuno et al. |
| 5,921,990 A | 7/1999 | Webb |
| 5,925,049 A | 7/1999 | Gustilo et al. |
| 5,961,499 A | 10/1999 | Bonutti et al. |
| 5,997,566 A | 12/1999 | Tobin |
| 6,007,537 A | 12/1999 | Burkinshaw et al. |
| 6,012,456 A | 1/2000 | Schuerch |
| 6,015,419 A | 1/2000 | Strome et al. |
| 6,019,767 A | 2/2000 | Howell |
| 6,022,350 A | 2/2000 | Ganem et al. |
| 6,024,746 A | 2/2000 | Katz |
| 6,056,754 A | 5/2000 | Haines et al. |
| 6,056,756 A | 5/2000 | Eng et al. |
| 6,059,817 A | 5/2000 | Bonutti et al. |
| 6,059,831 A | 5/2000 | Braslow et al. |
| 6,063,095 A | 5/2000 | Wang et al. |
| 6,077,270 A | 6/2000 | Katz |
| 6,077,287 A | 6/2000 | Taylor et al. |
| 6,086,593 A | 7/2000 | Bonutti |
| 6,090,122 A | 7/2000 | Sjostrom et al. |
| 6,096,043 A | 8/2000 | Techiera et al. |
| 6,099,531 A | 8/2000 | Bonutti |
| 6,099,532 A | 8/2000 | Florea |
| 6,102,850 A | 8/2000 | Wang et al. |
| 6,106,529 A | 8/2000 | Techiera |
| 6,118,845 A | 9/2000 | Simon et al. |
| 6,120,509 A | 9/2000 | Wheeler |
| 6,132,472 A | 10/2000 | Bonutti |
| 6,156,070 A | 12/2000 | Incavo et al. |
| 6,159,246 A | 12/2000 | Mendes et al. |
| 6,171,340 B1 | 1/2001 | McDowell |
| 6,174,321 B1 | 1/2001 | Webb |
| 6,185,315 B1 | 2/2001 | Schmucker et al. |
| 6,187,023 B1 | 2/2001 | Bonutti |
| 6,195,158 B1 | 2/2001 | Cadell et al. |
| 6,197,064 B1 | 3/2001 | Haines et al. |
| 6,198,794 B1 | 3/2001 | Peshkin et al. |
| 6,211,976 B1 | 4/2001 | Popovich et al. |
| 6,214,051 B1 | 4/2001 | Badorf et al. |
| 6,228,121 B1 | 5/2001 | Khalili |
| 6,258,127 B1 | 7/2001 | Schmotzer et al. |
| 6,277,136 B1 | 8/2001 | Bonutti |
| 6,290,703 B1 | 9/2001 | Ganem et al. |
| 6,290,704 B1 | 9/2001 | Burkinshaw et al. |
| 6,325,806 B1 | 12/2001 | Fox |
| 6,328,572 B1 | 12/2001 | Higashida et al. |
| 6,338,737 B1 | 1/2002 | Toledano et al. |
| 6,358,266 B1 | 3/2002 | Bonutti |
| 6,361,565 B1 | 3/2002 | Bonutti |
| 6,391,040 B1 | 5/2002 | Christoudias |
| 6,406,495 B1 | 6/2002 | Schoch et al. |
| 6,409,722 B1 | 6/2002 | Hoey et al. |
| 6,423,063 B1 | 7/2002 | Bonutti |
| 6,431,743 B1 | 8/2002 | Mizutani et al. |
| D462,767 S | 9/2002 | Meyer et al. |
| 6,458,135 B1 | 10/2002 | Harwin et al. |
| 6,468,280 B1 | 10/2002 | Saenger et al. |
| 6,468,289 B1 | 10/2002 | Bonutti |
| 6,478,799 B1 | 11/2002 | Williamson |
| 6,482,209 B1 | 11/2002 | Engh et al. |
| 6,500,181 B1 | 12/2002 | Portney |
| 6,503,267 B2 | 1/2003 | Bonutti et al. |
| 6,554,837 B1 | 4/2003 | Hauri et al. |
| 6,554,838 B2 | 4/2003 | McGovern et al. |
| 6,558,391 B2 | 5/2003 | Axelson, Jr. et al. |
| 6,575,982 B1 | 6/2003 | Bonutti |
| 6,602,259 B1 | 8/2003 | Masini |
| 6,620,181 B1 | 9/2003 | Bonutti |
| 6,632,225 B2 | 10/2003 | Sanford et al. |
| 6,635,073 B2 | 10/2003 | Bonutti |
| 6,673,077 B1 | 1/2004 | Katz |
| 6,676,662 B1 | 1/2004 | Bagga et al. |
| 6,695,848 B2 | 2/2004 | Haines |

| | | | |
|---|---|---|---|
| 6,702,821 B2 | 3/2004 | Bonutti | |
| 6,770,078 B2 | 8/2004 | Bonutti | |
| 6,979,299 B2 | 12/2005 | Peabody et al. | |
| 7,029,477 B2 | 4/2006 | Grimm | |
| 7,172,599 B2 | 2/2007 | Steffensmeier et al. | |
| 7,261,719 B1 | 8/2007 | Twomey et al. | |
| 7,488,324 B1 | 2/2009 | Metzger et al. | |
| 2001/0018589 A1 | 8/2001 | Muller | |
| 2001/0034554 A1 | 10/2001 | Pappas | |
| 2001/0037155 A1 | 11/2001 | Merchant | |
| 2002/0029038 A1 | 3/2002 | Haines | |
| 2002/0029045 A1 | 3/2002 | Bonutti | |
| 2002/0052606 A1 | 5/2002 | Bonutti | |
| 2002/0116023 A1 | 8/2002 | Fletcher et al. | |
| 2002/0173797 A1 | 11/2002 | Van Zile et al. | |
| 2002/0198529 A1 | 12/2002 | Masini | |
| 2002/0198531 A1 | 12/2002 | Millard et al. | |
| 2003/0028196 A1 | 2/2003 | Bonutti | |
| 2003/0060831 A1 | 3/2003 | Bonutti | |
| 2003/0100906 A1 | 5/2003 | Rosa et al. | |
| 2003/0100907 A1 | 5/2003 | Rosa et al. | |
| 2003/0130665 A1 | 7/2003 | Pinczewski et al. | |
| 2003/0171757 A1 | 9/2003 | Coon et al. | |
| 2003/0212403 A1 | 11/2003 | Swanson | |
| 2003/0216741 A1 | 11/2003 | Sanford et al. | |
| 2003/0220641 A1 | 11/2003 | Thelen et al. | |
| 2003/0225413 A1 | 12/2003 | Sanford et al. | |
| 2004/0039395 A1 | 2/2004 | Coon et al. | |
| 2004/0102785 A1 | 5/2004 | Hodorek et al. | |
| 2004/0138670 A1 | 7/2004 | Metzger | |
| 2004/0220583 A1 | 11/2004 | Pieczynski et al. | |
| 2005/0049603 A1 | 3/2005 | Calton et al. | |
| 2005/0113840 A1 | 5/2005 | Metzger et al. | |
| 2005/0149042 A1 | 7/2005 | Metzger | |
| 2005/0177170 A1 | 8/2005 | Fisher et al. | |
| 2006/0095049 A1 | 5/2006 | Zannis et al. | |
| 2006/0142774 A1 | 6/2006 | Metzger | |
| 2006/0142778 A1 | 6/2006 | Dees | |
| 2007/0083209 A1 | 4/2007 | Schenberger et al. | |
| 2007/0233140 A1 | 10/2007 | Metzger et al. | |
| 2007/0282451 A1 | 12/2007 | Metzger et al. | |
| 2009/0149859 A1 | 6/2009 | Metzger et al. | |
| 2010/0198224 A1 | 8/2010 | Metzger et al. | |

FOREIGN PATENT DOCUMENTS

| | | |
|---|---|---|
| DE | 337437 | 5/1921 |
| FR | 1111677 | 3/1956 |
| JP | 64-029266 | 1/1989 |
| JP | 2501806 | 6/1990 |
| JP | 3504337 | 9/1991 |
| JP | 7178114 | 7/1995 |
| WO | WO-8804912 | 7/1988 |
| WO | WO-8909028 | 10/1989 |
| WO | WO-96/07361 | 3/1996 |
| WO | WO-9729703 | 8/1997 |

OTHER PUBLICATIONS

"pfcSigma.RP-F, High Function Demands Rotation," brochure. (2006) DePuy Orthopaedics, Inc. 2 pages.

"Rotating Platform Knee Technology," tri-fold brochure. (2007) DePuy Orthopaedics, Inc. 2 pages.

"Rotating Platform: Proven," brochure. (2007) DePuy Orthopaedics, Inc. 2 pages.

"Rotating Platform: Unique," brochure. (2007) DePuy Orthopaedics, Inc. 2 pages.

"Sigma High Performance Partial Knee, Unicondylar Surgical Technique," brochure. (2008) DuPuy Orthopaedics, Inc. pp. 1-33.

"Sigma HP Partial Knee," product information sheet. (Feb. 4, 2009).

"Sigma® High Performance Instruments, A high performance knee system demands high performance instruments," advertisement. (2007) DePuy Orthopaedics, Inc. 1 page.

"Sigma® High Performance Instruments, Balanced Surgical Technique," brochure. (2008) DePuy Orthopaedics, Inc. pp. 1-49.

"Sigma® High Performance Instruments, Measured Resection Classic Surgical Technique," brochure. (2008) DePuy Orthopaedics, Inc. pp. 1-48.

"Sigma® High Performance Instruments, Measured Resection Fixed Reference Surgical Technique, Featuring the mini-subvastus approach," brochure. (2007) DePuy Orthopaedics, Inc. pp. 48.

"Sigma® High Performance Instruments, Product Rationale," brochure. (2007) Depuy Orthopaedics, Inc. 12 pages.

"The Freeman Samuelson Total Knee System," brochure, Biomet, Inc. (1994) 4 pages.

"The Sigma® High Performance Partial Knee: Potential to move more naturally," tri-fold brochure. (2009) DuPuy Orthopaedics, Inc. 2 pages.

"Total Knee Replacement," brochure. (2004) DePuy Orthopaedics, Inc. pp. 1-16.

"What Really Matters," brochure. (2006) DePuy Orthopaedics, Inc. 6 pages.

"Your New Rotating Platform Knee," tri-fold brochure. (2007) DePuy Orthopaedics, Inc. 2 pages.

International Search Report and Written Opinion mailed Jun. 3, 2005 for PCT/US04/00953 claiming benefit of U.S. Appl. No. 10/345,102, filed Jan. 15, 2003.

"AGC 3000 Intramedullary Surgical Technique Using PMMA Fixation," 1987, Biomet, Inc.

"AGC Distal Fem Cutter for Dr. Hardy," Biomet, Inc., Jun. 22, 1989.

"AGC Total Knee System, Intramedullary Without Distractor Surgical Technique," 1989, Biomet, Inc.

"AGC Traditional Surgical Overview", copyright 2001 Biomet Orthopedics, Inc.

"AGC-S Total Knee System, Surgical Technique for the AGC-S Total Knee System," 1992, Biomet, Inc.

"Anatomic Axial Alignment Instrumentation," 1994, Biomet, Inc.

"Hand Instruments", High Performance, Precision Series brochure by Arthrotek, copyright 2000.

"The AGC Revision Knee System Surgical Technique," 1997 Biomet, Inc.

AGC Total Knee System, Unicondylar Surgical Overview, Biomet, Inc. (4 pages).

Genus, brochure entitled "Uni Knee System," Biomet, Inc., Nov. 15, 1998.

Insall/Burstein II Modular Knee System by Zimmer, Inc. copyright 1989.

Keys, Graham W., "Reduced Invasive Approach for Oxford II Medial Unicompartmental Knee Replacement—Preliminary Study," The Knee, (1999) pp. 193-196.

McGinty, M.D., Operative Arthroscopy, Department of Orthopaedic Surgery, Medical University of South Carolina, Charleston, South Carolina, copyright 1991 by Raven Press, Ltd., (2 pages).

Microplasty™ minimally invasive knee instruments brochure, Surgical Technique for the Maxim®, Ascent™ and Vanguard™ Total Knee Systems, Biomet Orthopedics, Inc., Feb. 29, 2004.

MIS Minimally Invasive Solution—The M/G Unicompartmental Knee by Zimmer, 4 sheets.

MIS Minimally Invasive Solution The M/G Unicompartmental Knee Minimally Invasive Surgical Technique, by Zimmer, copyright 2000 (pp. 1-27).

Nex Gen Complete Knee Solution—Intramedually Instrumentation Surgical Technique—For the NexGen Cruciate Retaining & Legacy Posterior Stablized Knee—Publication date unknown, but before Aug. 1, 2001.

NexGen Complete Knee Solution—Extramedullary/Intramedullary Tibial Resector Surgical Technique—Publication date unknown, but before Aug. 1, 2001.

NexGen Complete Knee Solution—Multi-Reference 4-in-1 Femoral Instrumentation—Anterior Reference Surgical Technique—Publication date unknown, but before Aug. 1, 2001.

NexGen Complete Knee Solution—Surgical Technique for the LPS-Flex Fixed Bearing Knee—Publication date unknown, but before Aug. 1, 2001.

NexGen System Complete Knee Solution—Design Rationale—publication date unknown.

Orthopaedic Update, No. 18, The Fudger™—The Ultimate Weapon in the Femoral Referencing War, Biomet, Inc. (2 pages).

Scorpio! Single Axis Total Knee System—Passport Total Knee Instruments—Passport A.R. Surgical Technique by Sryker Howmedica Osteonics, Copyright 2000.

Simple Instruments Surgical Technique for the Knee, copyright 2000 Biomet, Inc.

Surgical Navigation for Total Knee Arthroplasty—Believed to have been presented at the American Academy of Orthopedic Surgeons in Feb. 2001.

The Oxford, brochure entitled "Unicompartmental Knee System", Biomet Orthopedics, Inc., Jul. 15, 2004.

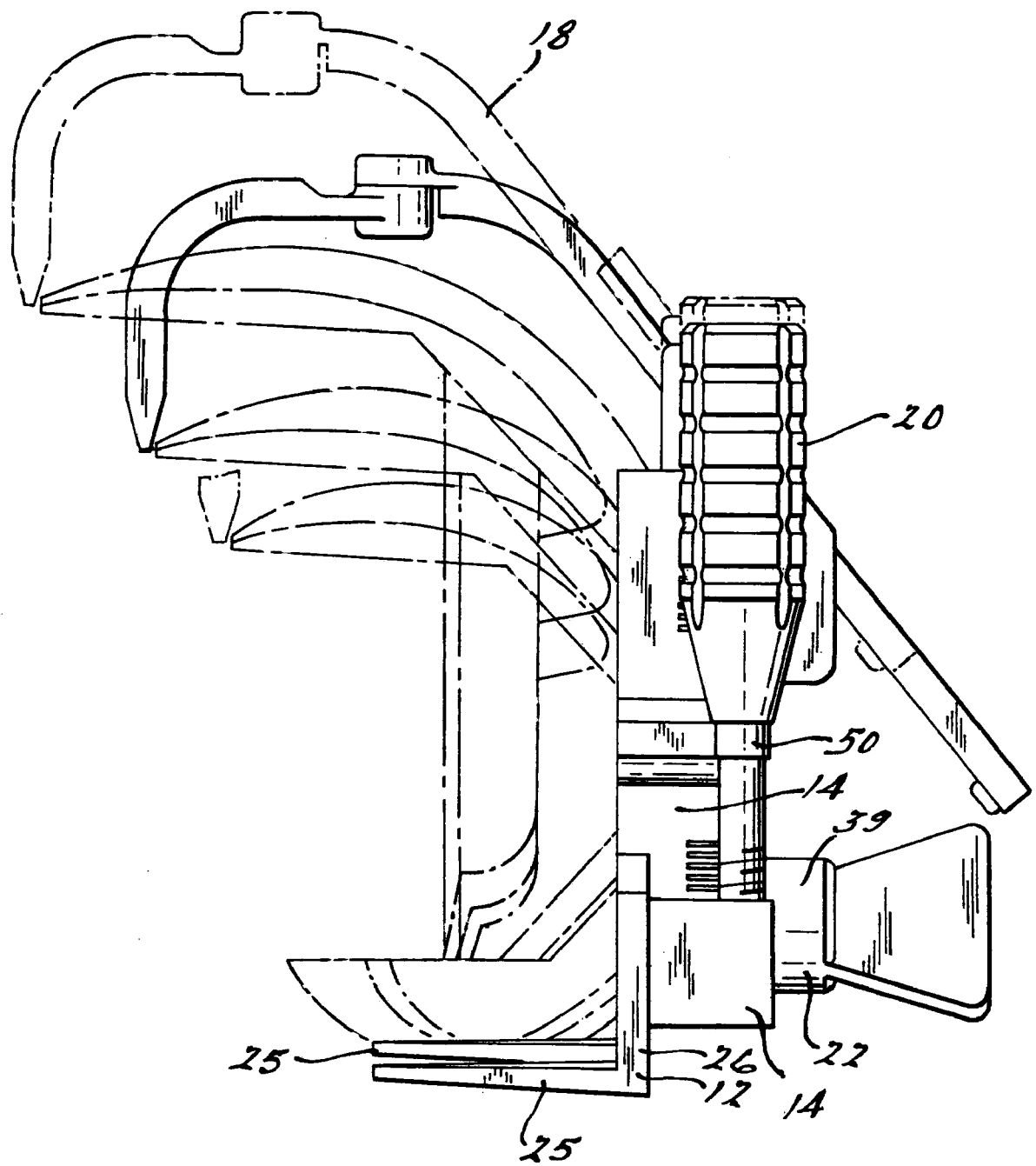

FEMORAL GUIDE FOR IMPLANTING A FEMORAL KNEE PROSTHESIS

CROSS-REFERENCE TO RELATED APPLICATIONS

This application is a continuation of U.S. patent application Ser. No. 10/730,456 filed on Dec. 8, 2003. The entire disclosure of the above application is incorporated herein by reference.

FIELD OF THE INVENTION

The present invention relates generally to the alignment hardware used in a surgical procedure and, more particularly, to an alignment hardware used in the implantation of a femoral prosthesis.

BACKGROUND OF THE INVENTION

The implantation of knee prosthetics require the distal end of the femur to be prepared to receive a femoral component of the knee prosthetic. This preparation generally requires the resection of various surfaces of the femur to ensure the proper coupling of the knee prosthetic to the resected surfaces. Various guides are known to assist the surgeon in locating cutting blades used to resect the femur.

The location and size of cuts to the femur generally correspond to internal surfaces within the femoral prosthetics. The location of the surfaces may change depending on the size of the prosthetics used. To this end, a femoral sizing guide is used to determine the size of the femoral prosthetic which will be implanted at the implantation site of the particular patient.

Femoral knee prosthesis are made available in a range of standard sizes. A femoral sizing guide is used to assist the selection of a standard sized femoral knee prosthetic which will best fit the requirements of a particular implantation site. The size and orientation of the implant is a function of kinematic and biomechanical considerations. In this regard, the femoral sizing guide is used to measure the condyles of the patient's femur and specifies the proper location of guiding apertures within the femur. As such, it is necessary to provide a reliable femoral sizing guide which is configured to allow the surgeon to determine the size and proper orientation of the femoral implant.

SUMMARY OF THE INVENTION

The present invention provides a femoral sizing guide which facilitates the selection and rotational orientation of the femoral prosthetic for a given resected femur. In this regard, the femoral sizing guide is provided having an extension portion configured to be placed adjacent to a posterior condyle surface of the femur. The extension portion is pivotally connected to a base portion at a first location and coupled to a rotation mechanism which is configured to rotate the extension portion with respect to the base. Slidably coupled to the base portion is a superstructure having a drilling guide. Further coupled to the superstructure is a graduated stylus which is configured to measure the location of an anterior condyle surface.

In another embodiment of the present invention, a femoral sizing guide is provided having an extension portion which is configured to engage a posterior surface of the condyle. The extension portion is pivotally coupled to a base portion at a first location, disposed between the exterior portion and the base is a worm gear configured to rotate the extension portion with respect to the base. A stylus is provided which is coupled to the base portion wherein the stylus measures the location of an anterior surface of a condyle.

In another embodiment of the present invention, a femoral sizing guide is provided having an extension portion pivotally coupled to a base portion. Disposed between the base portion and the extension portion is a worm gear which is configured to rotate the angle of the extension portion with respect to the base. Slidably coupled to the base is a superstructure which is configured to measure the location of an anterior side of the femur. Disposed between the superstructure and the base is an actuator configured to move the superstructure with respect to the base.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4 is a cross-sectional view of the worm gear mechanism shown in FIG. 2;

FIG. 5 represents a side view of the femoral sizing guide measuring a plurality of insert sizes;

DETAILED DESCRIPTION OF THE PREFERRED EMBODIMENT

The following description of the embodiment is merely exemplary in nature and is in no way intended to limit the invention, its application, or uses.

Figure 1:
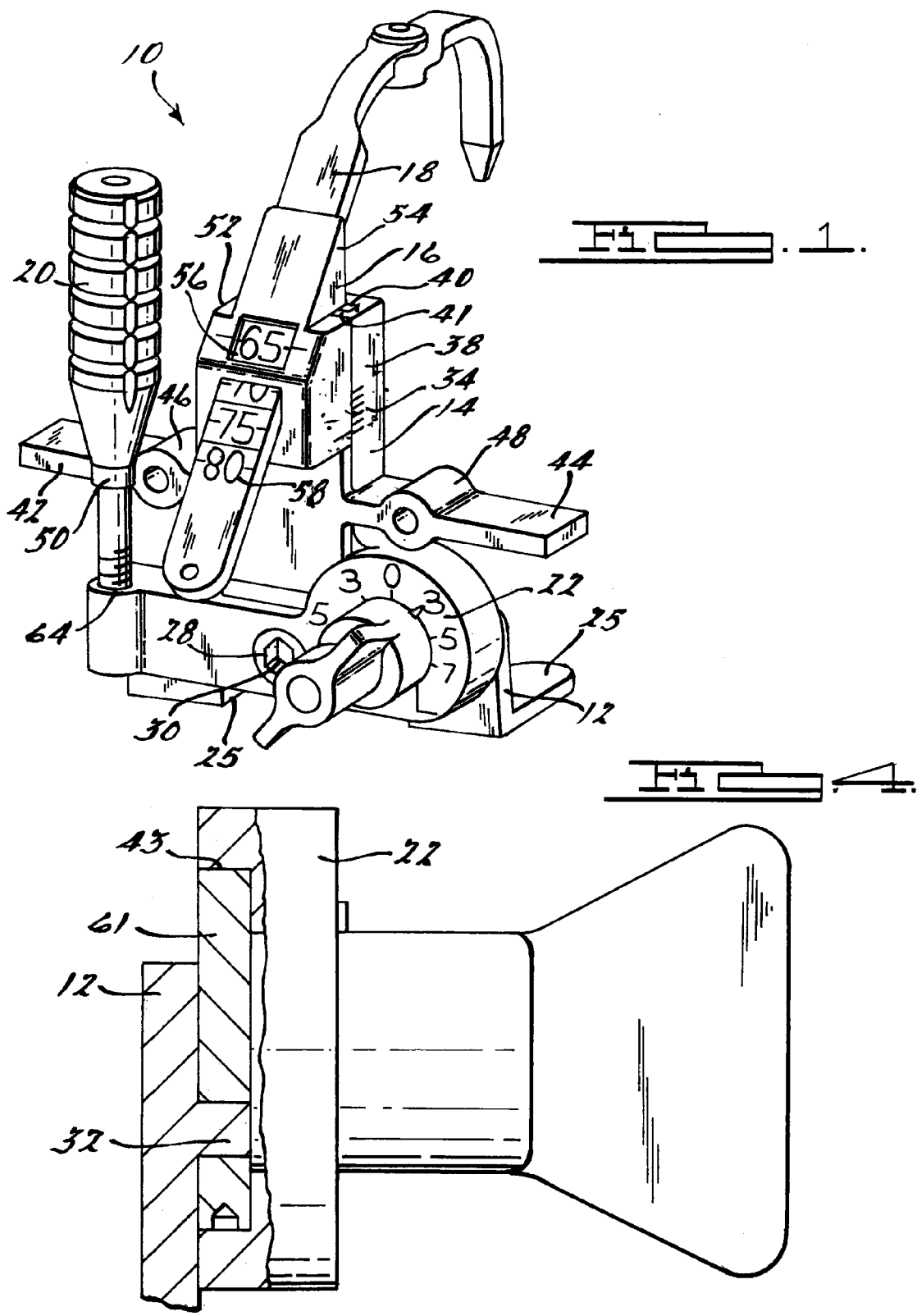
FIG. 1 represents a perspective view of the femoral sizing guide of the present invention.
Figure 2:
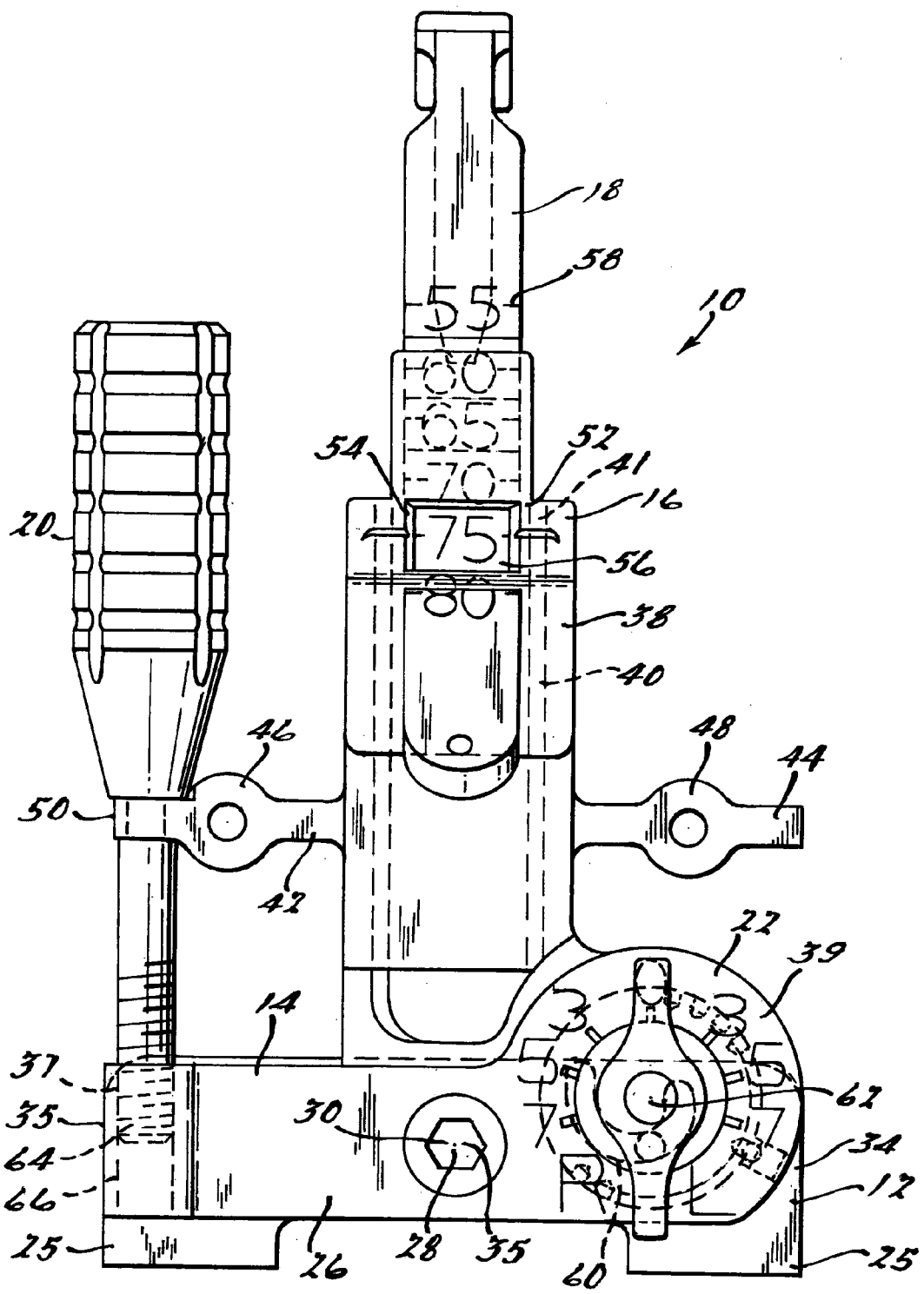
FIG. 2 represents a front view of the femoral sizing guide shown in FIG. 1.

Referring generally to FIGS. 1 and 2, a femoral sizing guide 10 according to the teachings of the present invention is shown. The femoral sizing guide 10 is generally formed of an extension portion 12, a base portion 14, a superstructure portion 16 having a corresponding graduated stylus 18, an actuator 20 disposed between the superstructure 16 and the base portion 14, and a worm gear 22. The femoral sizing guide 10 is configured to measure the size and general angular orientation of the condyles of a femur to allow a treating physician to interoperatively select a proper femoral prosthetic.

The feet 25 of the extension portion 12 use the posterior sides of the condylar surfaces as a reference. As the surfaces of the condyles can be degraded due to natural causes, their ability to function as a reference surface and, therefore, indexing plane can be degraded. As such, adjustability of the feet 25 can assist in the alignment of the sizing guide.

Figure 3:
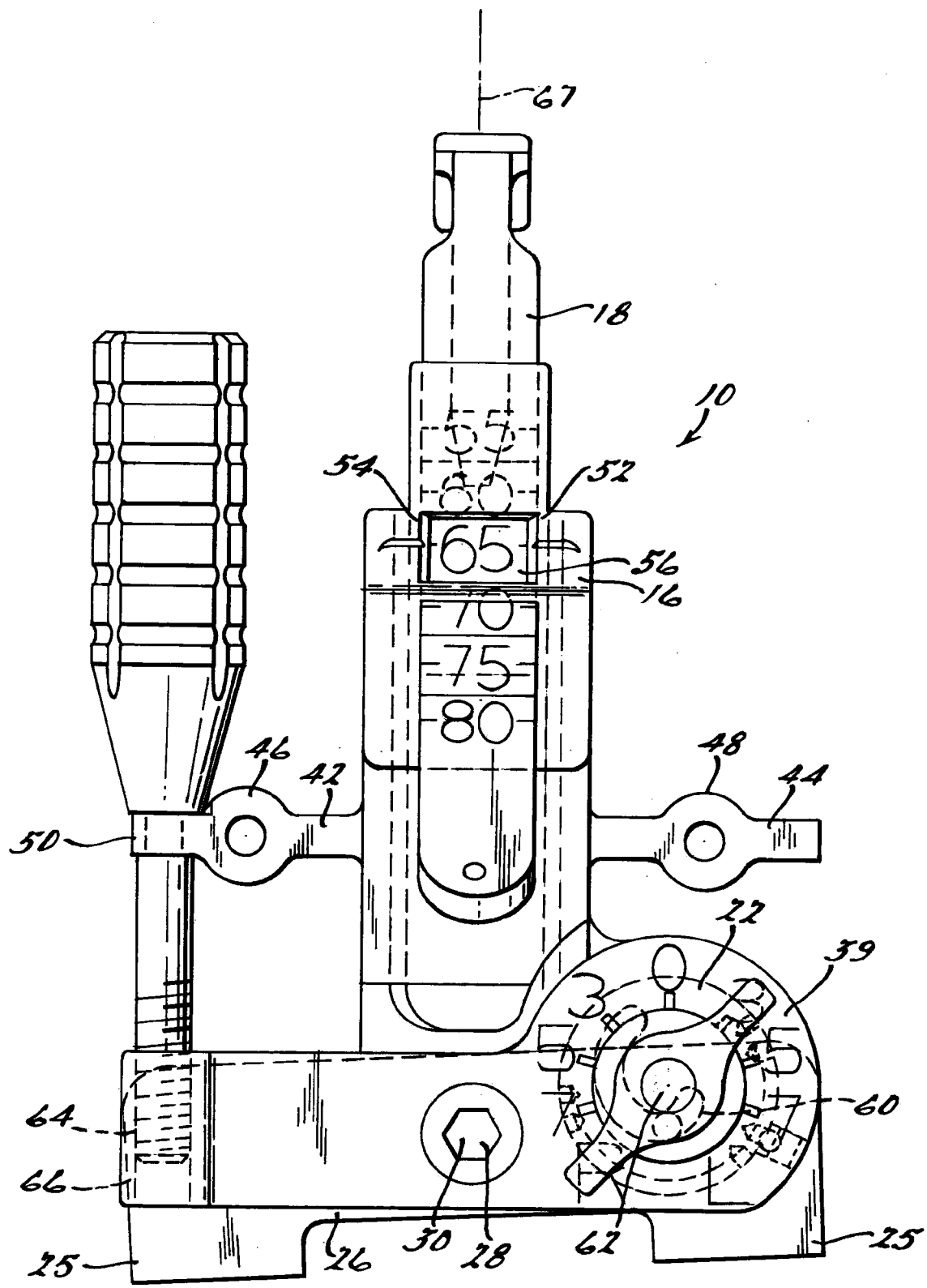
FIG. 3 represents a femoral sizing guide shown in FIG. 1 with the worm gear actuated.

As best seen in FIGS. 2 and 3, the extension portion has a pair of feet 25 coupled to a central member 26. The extension portion 12 is pivotally coupled to the base portion 14 at a central pivot point 28 through a pivot axis 30. Further disposed between the extension portion 12 and the base portion 14 is a worm gear 22 which functions to rotate the extension portion 12 and corresponding feet 25 about the pivot axis 30 in a predetermined and repeatable fashion. The extension portion 12 further has a depending pin or flange 32 which defines a first portion of the worm gear 22.

The base portion 14 has a body 34 having a body pivot point 35 which corresponds to the pivot axis 30. A body 34 defines a support flange 38 having a support flange track 40 which is configured to interface with a superstructure track 41. Defined on a first side 35 of the body 34 is a threaded coupling portion 37. The threaded coupling portion 37 is configured to be coupled to the actuator 20. A second side 45 of the body 34 defines a worm gear mount 39. The worm gear mount 39 defines an aperture 43 and further has a plurality of indexing gradations which will be used by a treating physician to determine the amount of rotation of the feet 25 with respect to the base portion 14 about pivot axis 30. It should be noted that the pivot axis 30 is offset a predetermined distance from the transepicondylar axis of the femur.

The superstructure 16 has a pair of depending side flanges 42 and 44 which define drilling guides 46 and 48. The first depending side flange 42 further defines a coupling mechanism 50 which is shown in the form of an aperture to rotatably support and guide the second actuator 20. The superstructure 16 further has a holding mechanism 52 which defines an indexed slot 54 which slidably receives the graduated stylus 18. The holding mechanism 52 further defines a window 56 which displays graduations 58 of the graduated stylus 18.

As best seen in FIG. 3, the extension portion 12 can be rotated about the pivot axis 30 by the rotation of the first actuator or worm gear 22. In this regard, the worm gear 22 defines an arcuate slot 60 which is rotatable about a gear pivot point 62. The arcuate slot 60 slidably holds the fixed worm gear pin 32. The rotation of the arcuate slot 60 about the coupling point 62 causes the rotation of the extension portion 12 with respect to the base portion 14. Similarly, it causes rotation with respect to the superstructure 16 and the stylus 18. The worm gear has a system of associated graduations which allow a treating physician to categorize the necessary rotation of the measurement guide about the central pivot axis 30.

The actuator 20 functions to translate the superstructure portion 16 with respect to the extension portion 12 or the base portion 14. In this regard, the rotation of the actuator 20 causes a threaded distal end 64 of the actuator 20 to rotate within a threaded hole 66 in the coupling portion 37 of the base portion 14. This causes the superstructure portion 16 and stylus 18 to translate in a second axis 67 away from or toward the base portion 14 and associated feet 25 of the extension portion 12. The movement causes translation of the drill guides 46 and 48 with respect to the feet 25 and the resected femur.

FIG. 4 represents a cross-sectional view of the worm gear 22. As seen, the extension portion 12 has a depending pin 32 which interfaces with the arcuate slot 60 defined in a first rotating member 61. The rotating member 61 and associated handle portion 63 are rotatably coupled to the worm gear mount 39 of the base portion 14. The worm gear mount 39 has a plurality of gradations which indicate the relative rotations of the extension portion 12 with respect to the base portion 14 and associated superstructure 16.

Figure 6:
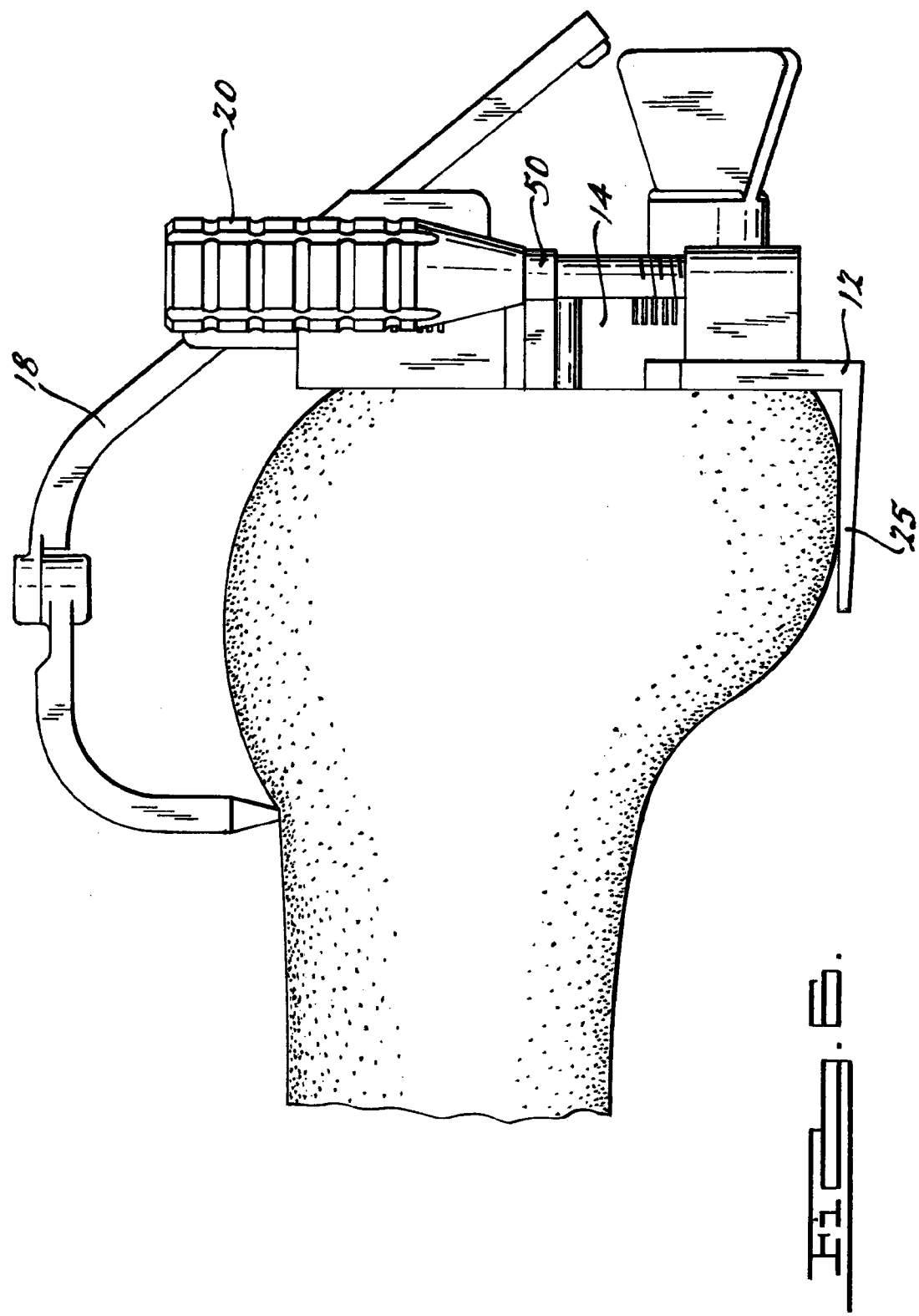
FIG. 6 is a side view of the femoral sizing guide coupled to a resected femur.

Shown in FIGS. 5 and 6, the graduated stylus 18 rests against the anterior cortex of the femur at an anterior/posterior location. Angular adjustment of the extension portion 12 with respect to the base portion 14 is made by rotating the worm gear 22 and adjusting the actuator 20 so as to allow for the proper standard size femoral implant to be used. In this regard, the adjustments allow the surgeon to properly position the drilling guides 46 and 48 so as to allow a proper positioning of the guide holes (not shown). The holes drilled using the drilling guides 46 and 48 are used to position a cutting guide (not shown) which is used to make cuts to form surfaces which correspond to internal planar surfaces on the interior surface of the femoral prosthetic 80.

As shown in FIGS. 3, 5, and 6, the feet 25 of the extension portion 12 are positioned adjacent to the posterior side of the femoral condyles. The location of the tip of the stylus 18 is adjusted by sliding the stylus 18 within the index slot 54 of the holding mechanism 52. Further adjustment can be made by adjusting the position of the superstructure 16 with respect to the extension portion by rotating the actuator 20.

At this point, the worm gear 22 is rotated so as to centrally locate the tip of the stylus 18 on top of the interior condyle surface. The treating physician reads values from the graduated stylus 18, actuator 20, and indexed worm gear 22 to select the appropriate femoral prosthetic. A pair of retaining holes are then bore into the resected femur using the drilling guides 46 and 48.

FIGS. 7-12 represent a second embodiment of the present invention. Shown is a modular system which allows a treating physician to interoperatively assemble the femoral sizing guide 10b. This allows the treating physician to use a rotatable foot portion 25a or a non-rotatable foot portion 25b. Additionally, the treating physician can utilize varying types of superstructure 16a or 16b.

Figure 7:
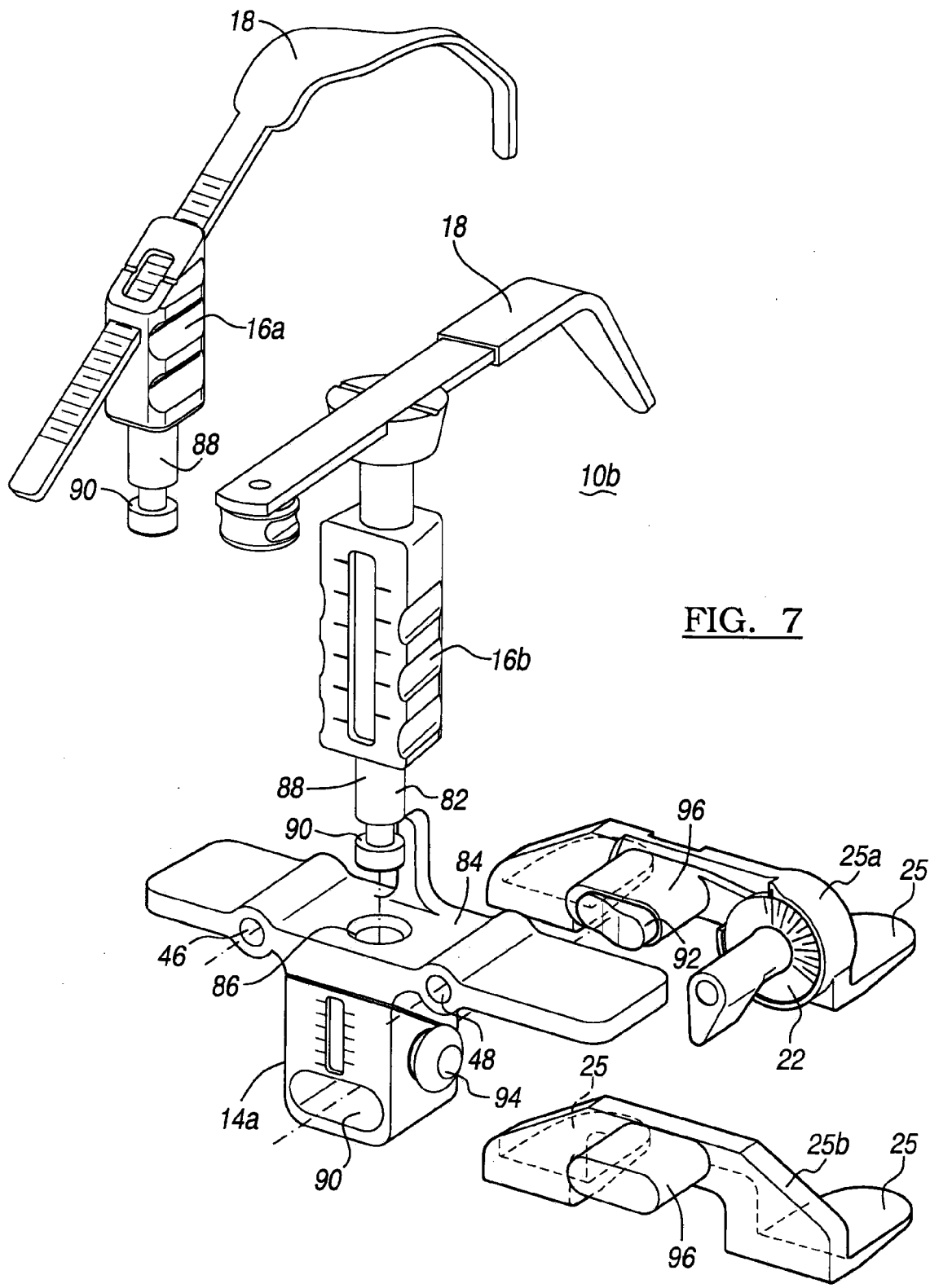
FIGS. 7 and 8 are exploded views of a femoral measurement guide according to another embodiment of the present invention.
Figure 8:
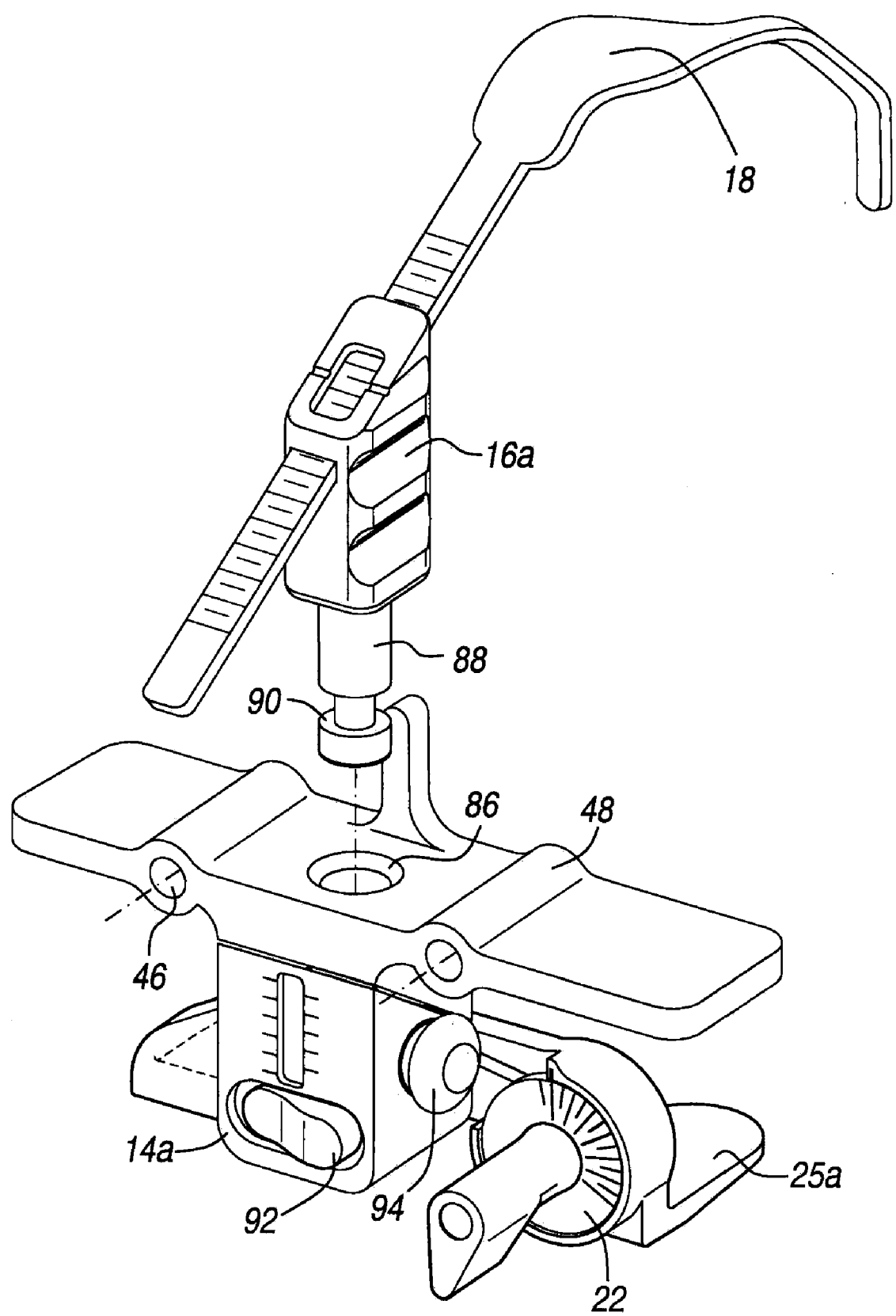

FIGS. 7 and 8 represent an exploded view of the femoral sizing guide 10b according to the teachings of a second embodiment of the invention. Shown is a base portion 14a which defines a coupling mechanism 82 for coupling either the first or second superstructure 16a or 16b to the top surface 84 of the base portion 14a. As shown, the coupling mechanism can take the form of an aperture 86 defined in the top surface 84 which is configured to fixably receive a post 88 formed on the superstructure 16a or 16b. The post 88 can optionally have a locking feature 90 which allows the post to be non-rotatably and yet releasably coupled to the base 14a.

Additionally, the base 14a defines a second coupling mechanism 90 which is configured to couple the base 14a to either one of the rotatable foot portion 25a or the non-rotatable foot portion 25b. The coupling mechanism 90 is shown as an elliptical bore defined in the base 14a. The elliptical bore 90 corresponds to an elliptical coupling structure defined on the foot portions 25a or 25b.

Components which are coupled to base portion 14a can be removed by releasing a spring loaded locking mechanism 92 defined on the elliptical structure on the foot portion 25a. It is envisioned the spring loaded locking mechanism 92 can be positioned on the base 14a.

Figure 10:
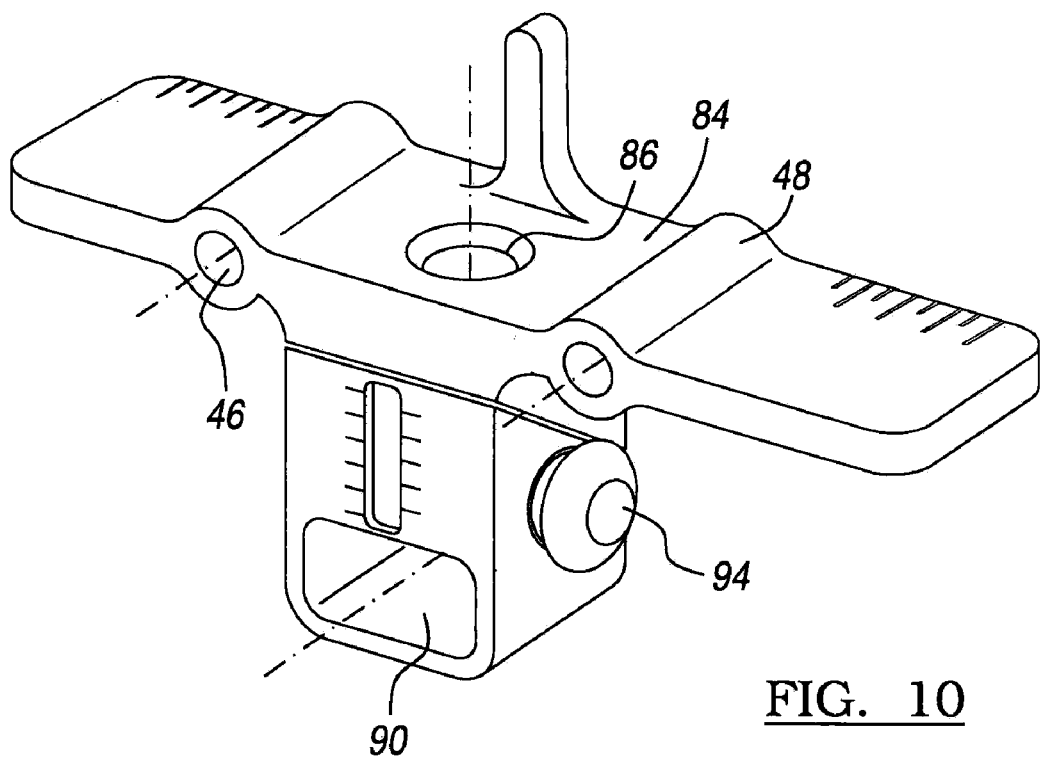
FIG. 10 is a base portion shown in FIG. 7.

As shown in FIGS. 7, 8, and 10, the base 14a is configured to allow translation of the drilling guides 46 and 48 with respect to the foot portion 25a. Shown is a knob 94, which is coupled to an internal gear (not shown) which causes the relative translation. It is envisioned that the actuator shown in FIG. 1 can additionally be used to adjust the relative location of the superstructure portion 16 with respect to the foot portion 25a.

Figure 9:
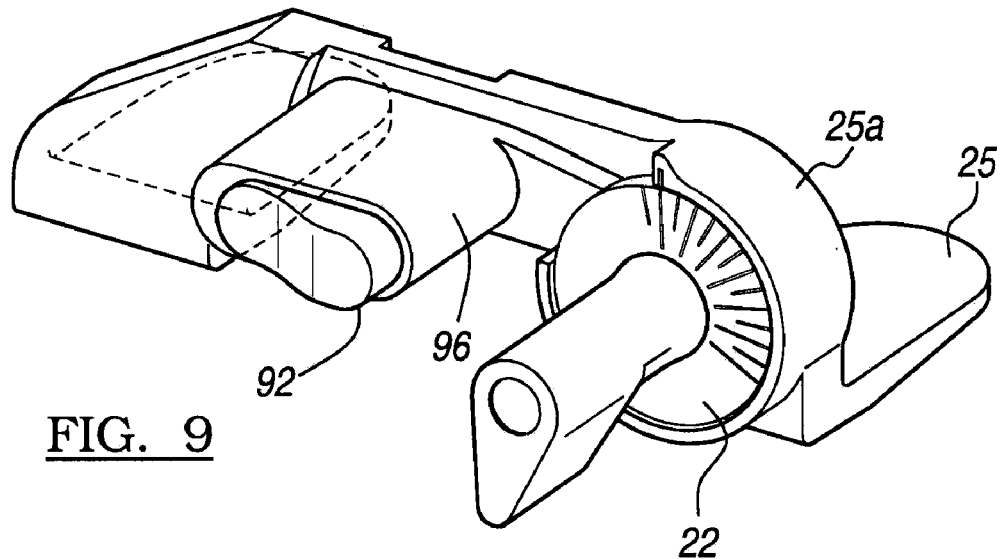
FIG. 9 is a modular adjustable foot portion shown in FIG. 7.

As best seen in FIG. 9, the adjustable foot portion 25a has a rotational mechanism which allows for rotation of the feet 25 with respect to the coupling mechanism 90. In this regard, the adjustable foot portion 25a has an oval post 96, about which the feet 25 are rotatably coupled. As described above with respect to the first embodiment, rotation of the worm gear 22 causes rotation of the feet with respect to the base portion 14a.

Figure 11:
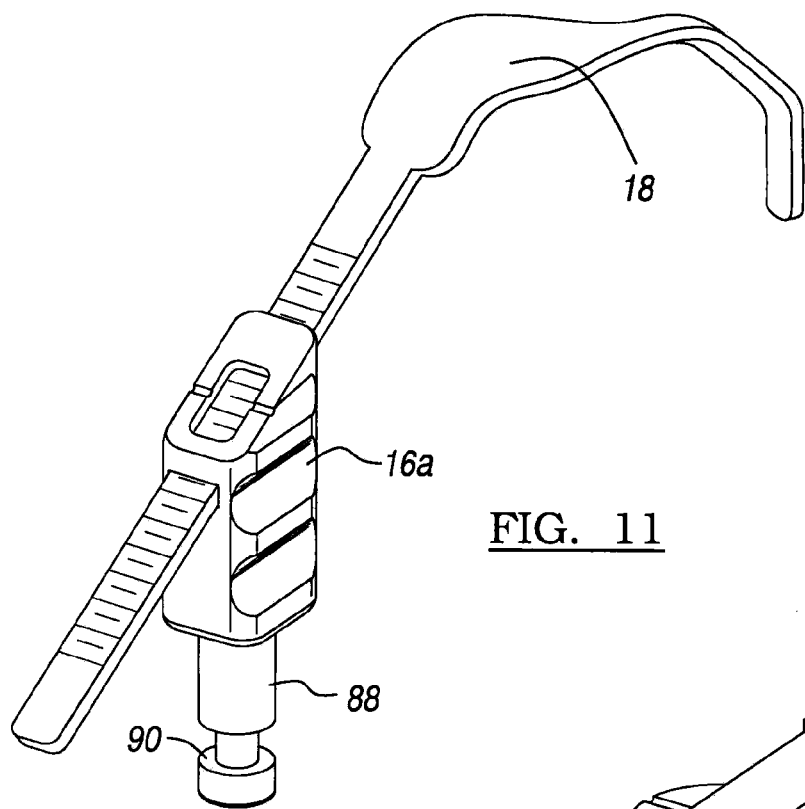
FIGS. 11 and 12 are modular superstructures shown in FIG. 7.
Figure 12:
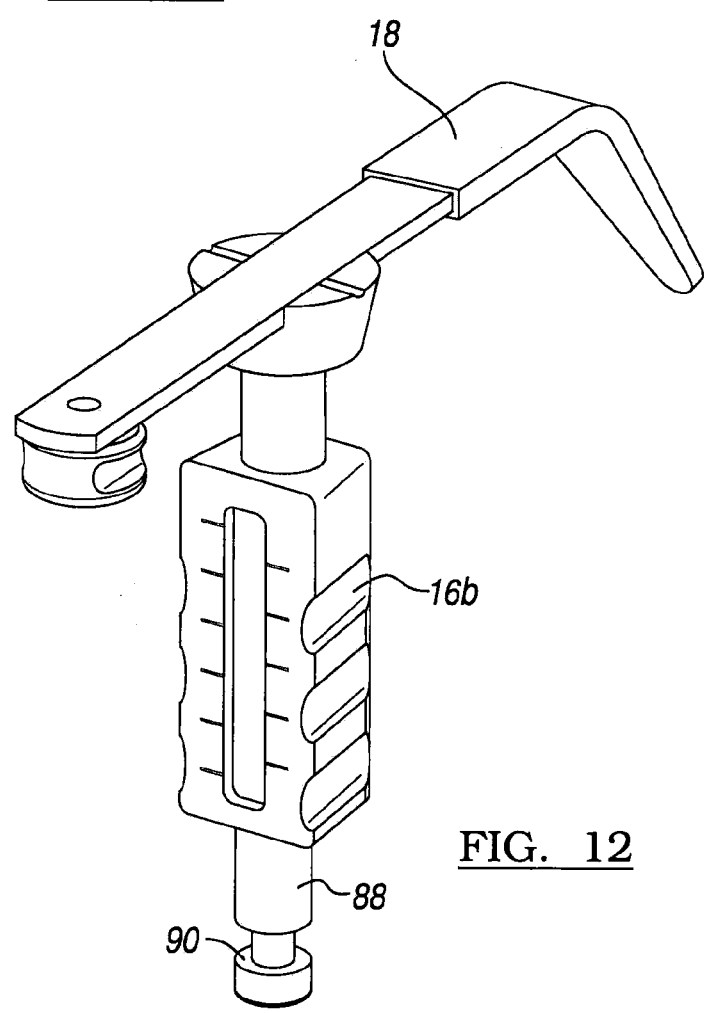

FIGS. 11 and 12 represent modular superstructure 16a and 16b. The superstructures are configured to be adjusted in a fashion which allows the treating physician to measure anatomical features of a resected bone. The location of the tip of the stylus 18 can be measured by vertical and horizontal adjustment of the superstructure 16b or by angular movement shown in superstructure 16a.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A femoral sizing guide which facilitates the selection of a femoral prosthetic, the femoral sizing guide comprising:
    an extension portion having an actuator bearing surface, said extension portion being configured to be placed adjacent to a posterior condyle surface of the femur;
    a base portion pivotally connected to the extension portion;
    a first actuator disposed between the extension portion and the base portion, the first actuator configured to apply force to the actuator bearing surface to rotatably displace the extension portion with respect to the base portion;
    a superstructure slidable relative to the base portion; and
    a stylus movable relative to the base portion and configured to be placed adjacent an anterior condyle surface of the femur.

2. The femoral sizing guide according to claim 1 wherein the first actuator includes a rotatable knob engagable by a user.

3. The femoral sizing guide according to claim 1 comprising a second actuator operable to displace the superstructure relative to the base.

4. The femoral sizing guide according to claim 1 wherein the superstructure defines at least one guide bore.

5. The femoral sizing guide according to claim 1 wherein the extension portion comprises a pair of feet configured to be positioned adjacent to a pair of posterior condyle surfaces of the femur.

6. The femoral sizing guide according to claim 5 wherein the extension portion is rotatably coupled to the base portion to allow rotation of the extension portion with respect to the base portion about a rotational axis.

7. The femoral sizing guide according to claim 5 wherein the rotational axis is disposed a predetermined distance from the first actuator.

8. The femoral sizing guide according to claim 6 wherein the rotational axis is located between the pair of feet.

9. A femoral sizing guide which facilitates the selection of a femoral prosthetic, the femoral sizing guide comprising:
    an extension portion configured to be placed adjacent to a posterior condyle surface of the femur;
    a base portion pivotally connected to the extension portion;
    a first actuator defining an arcuate bearing surface disposed between the extension portion and the base portion, the first actuator being configured to apply force to the extension portion and the base portion to rotatably displace the extension portion with respect to the base portion;
    a superstructure slidably coupled to the base portion; and
    a stylus movable relative to the extension portion and configured to be placed adjacent an anterior condyle surface of the femur.

10. The femoral sizing guide according to claim 9 further comprising indicia associated with the first actuator to measure displacement of the extension portion.

11. The femoral sizing guide according to claim 9 wherein the superstructure defines a slot configured to restrain the movement of the stylus.

12. A femoral sizing guide which facilitates the selection of a femoral prosthetic, the femoral sizing guide comprising:
    a foot portion configured to be placed adjacent to a posterior condyle surface of the femur;
    a base portion having a first coupling which is rotatably connected to the foot portion to allow relative rotation of the foot portion with respect to the base portion about a rotational axis, said base portion having a second coupling mechanism;
    a first actuator disposed between the foot portion and base portion, said first actuator being displaced from the rotational axis;
    a superstructure having a drilling guide, said superstructure slidably coupled to the second coupling;
    a stylus movable relative to the base portion and configured to be placed adjacent an anterior condyle surface of the femur; and
    a second actuator disposed between the superstructure and the base, said second actuator being configured to displace the superstructure with respect to the base portion.

13. The femoral sizing guide according to claim 12 wherein the second coupling is an elongated track.

14. The femoral sizing guide according to claim 12 wherein the foot portion comprises a pair of feet configured to be positioned adjacent to a pair of posterior condyle surfaces of the femur.

15. The femoral sizing guide according to claim 14 wherein the rotational axis is located between the pair of feet.

16. The femoral sizing guide according to claim 12 further comprising indicia to illustrate movement between the base portion and the superstructure.

17. A femoral sizing guide which facilitates the selection of a femoral prosthetic by measuring properties of a femur having posterior and anterior surfaces, the femoral sizing guide comprising:
    a member defining a posterior condyle engagement surface configured to be placed adjacent to a posterior surface of the femur;
    a base portion having a first coupling, said base portion being pivotally connected to the member about a pivot axis associated with the first coupling;
    a first actuator being displaced from the pivot axis and configured to apply forces to the member and the base portion to cause pivoting of the member with respect to the base portion;
    a superstructure moveable relative to the base portion and having a drilling guide; and
    a stylus movable with respect to the base portion, the stylus configured to be placed adjacent the anterior surface of the femur.

18. The femoral sizing guide according to claim 17 further comprising a second actuator being configured to displace the superstructure with respect to the base portion.

19. The femoral sizing guide according to claim 17 wherein the first actuator includes a rotatable knob that rotates relative to indicia on the base portion.

20. The femoral sizing guide according to claim 19 wherein the superstructure is linearly movable relative to the base portion.

21. The femoral sizing guide according to claim 17 wherein the member comprises a pair of feet configured to be positioned adjacent to the posterior condyle surface of the femur.

* * * * *